United States Patent
Mann

(10) Patent No.: US 8,353,595 B2
(45) Date of Patent: Jan. 15, 2013

(54) FUNDUS CAMERA

(75) Inventor: Dieter Mann, Kleinwallstadt (DE)

(73) Assignee: Dieter Mann GmbH, Mainaschaff (DE)

( * ) Notice: Subject to any disclaimer, the term of this patent is extended or adjusted under 35 U.S.C. 154(b) by 13 days.

(21) Appl. No.: 13/007,387

(22) Filed: Jan. 14, 2011

(65) Prior Publication Data

US 2011/0176109 A1   Jul. 21, 2011

Related U.S. Application Data

(60) Provisional application No. 61/295,864, filed on Jan. 18, 2010.

(30) Foreign Application Priority Data

Jan. 18, 2010   (DE) .................. 10 2010 004 884

(51) Int. Cl.
*A61B 3/14* (2006.01)
*A61B 3/10* (2006.01)

(52) U.S. Cl. ....................... 351/206; 351/221

(58) Field of Classification Search .......... 351/205, 351/206, 221

See application file for complete search history.

(56) References Cited

U.S. PATENT DOCUMENTS

| | | |
|---|---|---|
| 3,936,844 A | 2/1976 | Matsumura |
| 3,943,329 A | 3/1976 | Hlavac |
| 3,944,341 A | 3/1976 | Pomerantzeff |
| 3,954,329 A | 5/1976 | Pomerantzeff |
| 4,023,189 A | 5/1977 | Govignon |
| 4,200,362 A | 4/1980 | Pomerantzeff |
| 5,608,472 A | 3/1997 | Szirth et al. |
| 5,695,492 A | 12/1997 | Brown |
| 5,966,196 A | 10/1999 | Svetliza et al. |
| 2007/0030448 A1 | 2/2007 | Biernat et al. |

FOREIGN PATENT DOCUMENTS

| | | |
|---|---|---|
| DE | 42 32 280 A1 | 3/1994 |
| DE | 103 49 091 A1 | 5/2005 |
| WO | 2004/091362 A2 | 10/2004 |

*Primary Examiner* — Jack Dinh
(74) *Attorney, Agent, or Firm* — McDonnell Boehnen Hulbert & Berghoff LLP

(57) ABSTRACT

A hand camera for photographing an eye fundus is provided. The camera consists of a tube (3c), a camera housing (3a, 3b), which camera housing is attached to one end (3d) of the tube in a light-tight way, a camera device (4) that is able to record images by means of a two-dimensional optical sensor or a photographical film and that is accommodated in the camera housing (3a, 3b), a telephoto lens (5) that is arranged in the beam path of the light that is reflected from the eye fundus, which is accommodated in the camera housing (3a, 3b), a wide-angle lens (2), which is arranged in the beam path of the light that is reflected from the eye fundus at the other end (3e) of the tube (3c), and a light supplying device (1) consisting of a homogeneous trans-luminescent material, wherein the light supplying device (1) is arranged with respect to the tube (3c) in such a way that for a sufficient approach of the other end (3e) of the tube (3c) to the eye to be examined the light supplying device touches the sclera of the eye, provided that the center of the wide-angle lens is aligned with the center of the pupil.

11 Claims, 2 Drawing Sheets

FUNDUS CAMERA

CROSS-REFERENCE TO RELATED APPLICATIONS

The present application is a non-provisional application of U.S. Provisional Application Ser. No. 61/295,864, filed on Jan. 18, 2010. The present application also claims priority to German Application No. 102010004884.4, filed on Jan. 18, 2010. The entire contents of each of these applications are incorporated by reference herein.

BACKGROUND OF THE INVENTION

The present invention refers to a fundus camera for an imaging of the eye fundus. In particular, the invention refers to a fundus camera having compact dimensions, which can be offhand held in the hand.

The basic setup of a fundus camera consists of a multistage optical system, in which a wide-angle lens that is positioned in close proximity to the eye creates an intermediate image, which intermediate image is mapped onto a film or a CCD array by further optical components. Here, the necessity of bringing illumination light into the eye is a problem that always occurs, when the eye fundus is observed.

Usually the illumination light will enter the eye through the pupil. However, here the problem is met that there are reflexes at the refracting media in the eye, which reflexes interfere with the observation. U.S. Pat. No. 3,944,341 therefore describes a fundus camera, in which, though the light enters through the pupil, a reflection at the lens of the eye is avoided by choosing a ring-shaped illumination by means of optical fibres such that the edge region of the pupil is used for the illumination. In the document two elaborately designed light fibre rings are used for the illumination. However, as this kind of illumination is elaborate, often the front lens that is positioned close to the eye is also used for introducing the illumination light, as it is for example described in U.S. Pat. No. 3,936,844. Such a design, however, again results in a complex optical design, because the illumination light path and the imaging light path are close to each other. Thereby, the eye fundus observation device and camera become very bulky.

Due to the above described problems when using a trans-pupillary illumination, it was suggested in the prior art such as in U.S. Pat. No. 3,954,329 to illuminate the fundus through the sclera. However, this kind of illumination is rather unusual up to nowadays, though document U.S. Pat. No. 3,954,329 was already published in 1976. This might be related to the fact that for a trans-illumination of the sclera the luminous intensity must be high and out of this reason it is not possible to use a light fibre ring. Hence, in devices of the prior art, in which a trans-scleral illumination is used, usually the light is punctually radiated through the sclera by means of a fibre bundle (see for example U.S. Pat. No. 3,943,329). In doing so, it is necessary to radiate through the sclera at more than one position in order to homogenously illuminate the eye fundus. The necessary installation of more than two fibre bundles that results makes the fundus camera bulky.

In view of the above described problems it is an object of the present invention to provide a fundus camera that has a compact design, so that it can be held freely with one hand.

BRIEF SUMMARY OF THE INVENTION

The object is achieved by a hand camera according to claim 1. Further improvements of the invention are described in the dependent claims.

By the invention it becomes possible to build a mobile fundus camera having a large angular range of approximately 100° or more. The mobility of the camera, which can be operated with one hand, saves time and costs, in particular when patients have to be examined, who are treated in hospitals outside of the ophthalmological departments. Such a mobile camera, however, has a remarkable advantage also for premature infants: premature infants are difficult to examine, because they can only be transported cost-intensively and with an increased risk due to the incubator. Thus, a re-location of a premature infant to an ophthalmological department, where a stationary fundus camera can be used, turns out to be pretty laboriously. This problem can be solved by the camera according to the invention.

BRIEF DESCRIPTION OF THE SEVERAL VIEWS OF THE DRAWINGS

In the following, preferred embodiments of the invention are described by making reference to the drawings.

DETAILED DESCRIPTION OF THE INVENTION

Figure 1:
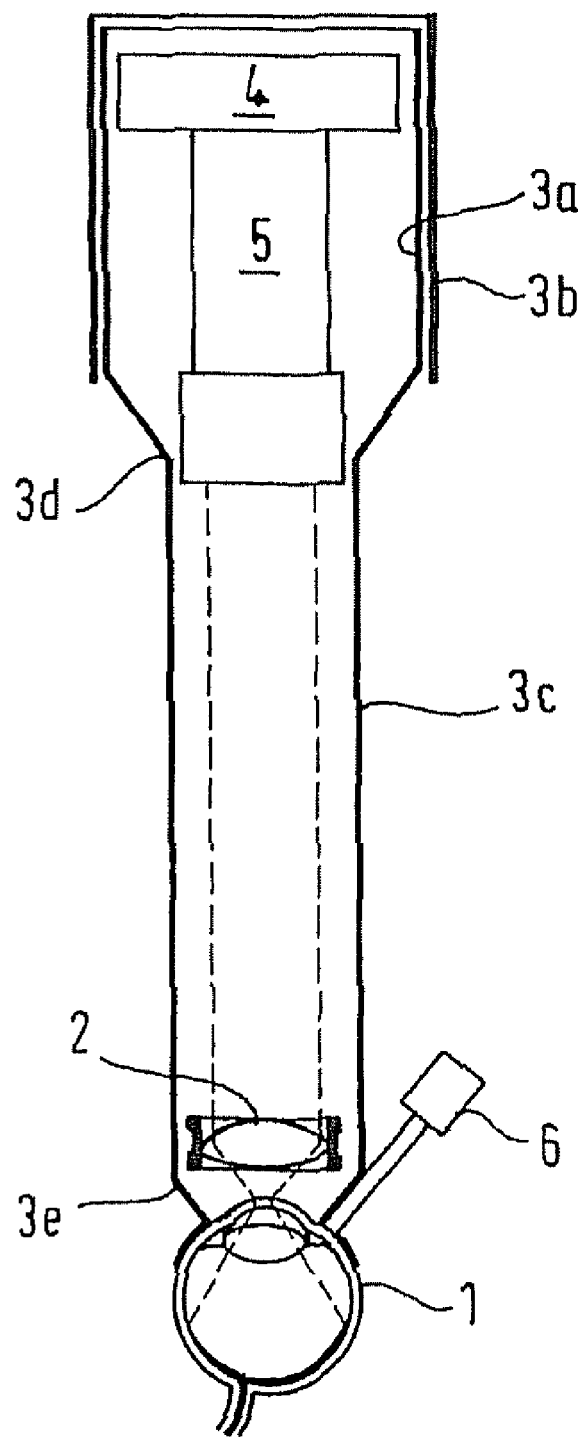
FIG. 1 shows a hand camera according to the invention, in which the wide-angle optics has no direct contact to the eye during the recordings.

The camera according to the invention comprises a tube $3c$ having a wide-angle lens 2 attached to the end $3e$ facing the eye to be examined. A telephoto-lens 5 and a camera 4 are attached at the end $3d$ of the tube facing away from the eye to be examined. The telephoto-lens 5 and the camera 4 are surrounded by a housing $3a$, $3b$, which is connected in a light-tight way with the tube $3c$. As can be seen in FIG. 1, the optics that is used is very simple. Basically the inner space of the tube $3c$ is empty. The virtual image that is generated by the wide-angle lens 2 is projected by the telephoto-lens 5 onto a two-dimensional optical sensor such as a CCD (charge coupled device) sensor or an APS sensor (active pixel sensor or CMOS sensor) or else onto a photographic film.

The camera may be a compact digital camera, which is pretty similar to a digital camera that is offered on the market for private consumers. The same applies to the telephoto-lens 5.

In order to change the focus either a commercially available zoom lens can be used or else a camera housing $3a$, $3b$, as it is represented in FIG. 1, is used. FIG. 1 shows that the camera may be connected to an upper housing part $3b$, which covers a lower camera housing part $3a$, which is connected to the tube $3c$, like a hood. Here, the lower camera housing part $3a$ has the shape of a cylindrical short pipe that is open to the top. When the upper camera housing part $3b$ is moved with respect to the lower camera housing part $3a$ in a direction of the longitudinal axis of the tube $3c$, then as a result the distance between the telephoto-lens 5 and the wide-angle lens 2 can be changed and thereby the focus can be changed. It should be noted that an operator of the camera can look through a view finder or onto a monitor that is attached to the backside of the camera in a similar way to commercially available cameras, wherein neither a view finder nor a monitor are shown in FIG. 1 out of simplicity reasons.

In the present invention the eye fundus is illuminated trans-sclerically. For this purpose a cylindrical ring attachment 1 out of a trans-luminescent material is attached to the end $3e$ of the tube $3c$ that is facing the eye. This ring attachment, which serves as a light supplying device, is put onto the eye concentrically to the cornea close to the limbus, so that the attachment rests on the eye on the sclera outside of the pupil. Light can be supplied to the ring attachment 1 from a light source 6. This may be effected for example by means of optical fibres that are coupled to the sidewall of the ring attachment 1. For example, a short pipe out of the trans-luminescent material of the ring attachment 1 may protrude from the sidewall of the ring attachment 1. Then an appropriate coupling device for attaching or screwing a cable that contains the light-conducting fibres is affixed on this short pipe.

As the eye has a curvature and as the ring attachment 1 rests on the eye with its face side on the eye, it is advantageous to have a surface area of the face side, which does not form a right angle with the longitudinal axis of the tube 3c. For example, the outer edge of the ring may further protrude towards the eye than the inner edge. Ideally, the face surface of the ring attachment additionally has a curvature, which curvature is adapted to the curvature of an average eye.

For the light guidance the ring attachment utilizes a total reflection of the light at the interface between the ring material and the surrounding air. Thus, the light is shone uniformly through the ring attachment and ideally is shone annularly through the sclera.

The ring attachment 1 may be made from a trans-luminescent plastic material or from glass. By using such a ring attachment, which is made from a homogenous material, a higher luminous intensity is obtained compared to a light fibre ring. Among other things this is due to the fact that the light fibres have a total area that is much smaller than the total area of the ring attachment. While light-guiding fibres usually have a diameter of a few 100 μm, the wall thickness of the ring attachment may be a few mm. Furthermore, by the selection of a particular ring material losses in the light conduction can be minimized.

Compared to the use of light-guiding fibres there is still a further advantage when using such a ring attachment:

Light-guiding fibres are known to heat up very much due to the heat conduction of the material. This may lead to a damage of the cells of the connective tissue in the eye, onto which the light-guiding fibres of the prior art are put when the temperature exceeds 42° C. In the invention such a heating-up is avoided already due to the larger contact surface at the eye. Moreover, by a selective choice of the material, a too excessive heating-up of the face surfaces of the ring attachment that are resting on the eye can be avoided. For example, borosilicate glass 3.3 may be used as ring material, which material blocks short-wave and long-wave portions of the radiation. In order to avoid damages, it is in any case advantageous to choose a diameter of the ring attachment 1 such that the ring attachment 1 rests on a position of the sclera that contains as few blood vessels as possible, when the pipe 3c is centrical to the pupil. For example, the diameter of the ring attachment might be chosen such that the distance between the position at which the ring attachment rests on the sclera and the limbus is approximately 2 mm.

By the fundus camera according to the invention a mobile hand camera is provided. In particular, such a camera might be held by the operator in his hand during the examination without the need of having to use a camera tripod. Ideally, the use of the camera is not much more complicated than the use of an ordinary digital camera. A red cast of the pictures that usually appears in a trans-scleral illumination can be computationally eliminated by the camera software after a digitalization. Thereby, complicated optics or various colour filters in the illumination light path in order to correct the colour are avoided.

The trans-scleral illumination has the decisive advantage that there are no problems with reflections at the lens of the eye. Furthermore, it is also a decisive advantage that examinations are possible even for small pupil diameters or pathological changes of the lens that make a trans-pupillar illumination impossible. For example, the formation of tumors may make impossible an illumination through the edge region of the pupil. As was already mentioned in the beginning, the camera is particularly suitable for an examination of premature infants. In order to make this possible, simply a ring attachment 1 having a smaller diameter and a steeper radius than the diameter and radius that are provided for adults have to be selected. "Steeper radius" here means the following: due to the larger curvature of the small eye of the premature infant the face surface of the ring attachment is formed such that the outer edge of the ring protrudes towards the eye to a larger extent than in the case of the ring attachment for adults.

Finally, the trans-scleral illumination makes it possible to illuminate the whole fundus, which is not possible in that way for a trans-pupillar illumination due to the limited diameter of the pupil. As a result, for a corresponding selection of the wide-angle lens 2 field viewing angles up to 165° are possible. In conjunction with FIG. 1 a ring attachment 1 was described that completely surrounds the pupil. The reason for such a complete surrounding of the pupil is a supply of the illumination light that is as uniform as possible. Of course the illumination light can also be trans-illuminated through the sclera at several positions around the pupil that are separated from each other. For example, the face surface of the ring attachment that is put onto the eye, may have recesses. In an extreme case these recesses may even take up most of the wall surface of the ring attachment. Thereby, the ring attachment 1 can rest on the sclera e.g. at six, five, four, three or even only two positions. Of course, the positions at which the ring attachment 1 touches the sclera preferably should have the same distance to each other in a circumferential direction around the pupil.

Of course, it is also possible to use a lens system or an optics having further elements instead of a wide-angle lens 2. However, the simpler such a wide-angle optics 2 and the fewer components it has, the smaller is the weight of the hand camera. The term "wide-angle optics" here shall comprise also optics that consist only of a singular wide-angle lens.

Figure 2:
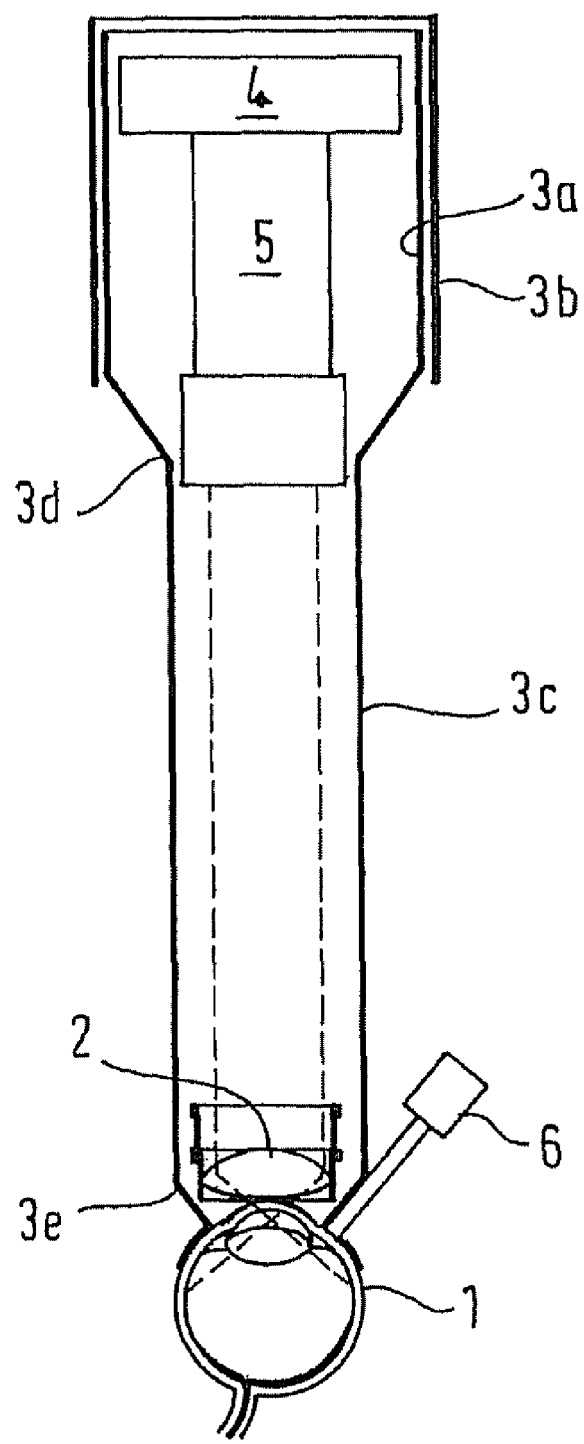
FIG. 2 is a hand camera according to the invention, in which the wide-angle optics touches the cornea during the recordings.

The wide-angle optics 2 that is arranged at the end 3e of the tube 3c that is facing the eye, may be arranged with respect to the face surface of the ring attachment 1 that shall be put onto the eye in such a way, that the wide-angle optics 2 is put onto the cornea of the eye simultaneously with the ring attachment hitting the sclera (indirect ophthalmoscopy, see FIG. 2). However, the wide-angle optics can also be arranged in the tube 3c such that it has a certain distance to the end 3e of the tube 3c that is facing the eye (see FIG. 1). In an ideal case the wide-angle optics 2 can be moved along the longitudinal axis of the tube 3c.

In a further embodiment of the invention there is no ring attachment 1 and the illumination light is supplied via a rod made of a trans-luminescent homogeneous material, wherein the rod is put onto a part of the sclera. Due to the high luminous intensity resulting from the use of such a light rod, provision can be made for a sufficient illumination of the eye fundus, though the sclera is trans-illuminated only at one point. Furthermore, the light rod may consist of the same materials as the ring attachment 1. The ring attachment 1 as well as the light rod may be covered by a light-reflecting material such as a silver layer or a metal pipe in order to improve the light-conducting ability.

According to a variant of the invention the light rod or the ring attachment can be moved independently from the tube 3c. In such a case only the light rod or the ring attachment are put onto the eye while the tube 3c with the wide-angle optics is held at a certain distance to the eye. Here, a mounting of the camera to a cross slide may be advantageous, because one hand is needed for the positioning of the light rod or the ring attachment.

In general it is advantageous, if the hand camera can also be mounted on a cross slide. When the cross slide is mounted at a height-adjustable table, a stationary unit is obtained, when the hand camera is fixed at the cross-slide. With such a stationary unit photos or movies at a sitting patient can be made. For example, for tumor patients it is important that the recordings are made at a sitting patient as well as at a lying patient. The recordings in a lying condition then are made with the hand camera, which is not mounted at a cross-slide. Furthermore, it is possible to connect the camera to a monitor via a cable, so that it is possible to view the camera picture on the monitor.

It is finally noted that the use of the term "cylinder" in the present application is not limited to a circular cylinder. Rather, the term "cylinder" is used in a mathematical sense and generally includes bodies that are limited by two parallel plane surfaces having an arbitrary shape and by a lateral surface that is connecting these surfaces. However, in particular this term shall designate any straight cylinder, in which the lateral surface is perpendicular to the bottom surface and the top surface.

The invention claimed is:

1. A hand camera for photographing an eye fundus comprising:
   a tube,
   a camera housing, that is attached in a light-tight way at one end of the tube,
   a camera device, that is able to record images by means of a two-dimensional optical sensor or a photographic film and that is accommodated in the camera housing,
   a telephoto lens arranged in a beam path of light that is reflected by the eye fundus, the telephoto lens being accommodated in the camera housing,
   a wide-angle optics that is arranged in the beam path of the light that is reflected from the eye fundus at the other end of the tube, and
   a light supplying device, which consists of a homogeneous trans-luminescent material, wherein the light supplying device is able to be put onto the sclera of the eye to be examined for a trans-scleral illumination of the eye fundus.

2. The hand camera according to claim 1, wherein the light supplying device is arranged with respect to the tube in such a way, that the light supplying device touches the sclera of the eye when the other end of the tube is sufficiently approached to the eye to be examined, provided that the centre of the wide-angle optics is aligned with the centre of the pupil.

3. The hand camera according to claim 1, in which the light supplying device is a light rod.

4. The hand camera according to claim 1, in which the light supplying device is a ring attachment shaped like a hollow cylinder, the ring attachment being attached to the other end of the tube such that the ring attachment can be put onto the sclera of the eye with a face surface being concentric to the pupil.

5. The hand camera according to claim 4, in which the ring attachment has at least one recess at the face surface, which face surface is to be put onto the sclera, wherein the recess is formed such that the face surface consists of a plurality of partial surfaces.

6. The hand camera according to claim 5, in which the at least one recess of the face surface is formed in such a way that the face surface consists of a plurality of individual partial surfaces, which have a distance to each other.

7. The hand camera according to claim 1, in which the homogeneous trans-luminescent material consists of glass or a plastic.

8. The hand camera according to claim 7, in which the homogeneous, trans-luminescent material is a borosilicate glass 3.3.

9. The hand camera according to claim 1, in which the light supplying device is covered by a layer that is reflecting to the inside of the light conducting device.

10. The hand camera according to claim 1, in which the wide-angle optics is arranged in such a way that when the light supplying device is put onto the sclera, the wide-angle optics touches the cornea of the eye when the light supplying device touches the sclera.

11. The hand camera according to claim 1, in which the wide-angle optics is arranged inside of the tube and in which the position of the wide-angle optics in the tube can be varied along the longitudinal axis of the tube.

* * * * *